United States Patent
Sano et al.

[11] Patent Number: 6,099,466
[45] Date of Patent: *Aug. 8, 2000

[54] FLUORESCENCE DIAGNOSIS ENDOSCOPE SYSTEM

[75] Inventors: Hiroshi Sano; Rensuke Adachi, both of Tokyo, Japan

[73] Assignee: Asahi Kogaku Kogyo Kabushiki Kaisha, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/966,581

[22] Filed: Nov. 10, 1997

Related U.S. Application Data

[63] Continuation of application No. 08/531,921, Sep. 21, 1995, abandoned.

[30] Foreign Application Priority Data

| Sep. 21, 1994 | [JP] | Japan | 6-226521 |
| Sep. 21, 1994 | [JP] | Japan | 6-226522 |
| Sep. 21, 1994 | [JP] | Japan | 6-226523 |
| Sep. 21, 1994 | [JP] | Japan | 6-226524 |

[51] Int. Cl.⁷ .............................................. A61B 1/06
[52] U.S. Cl. ......................... 600/160; 600/178; 600/109
[58] Field of Search .................................. 600/109, 118, 600/160, 178, 181, 407, 476, 478

[56] References Cited

U.S. PATENT DOCUMENTS

| 4,556,057 | 12/1985 | Hiruma et al. | 128/665 |
| 4,768,513 | 9/1988 | Suzuki | 128/665 |
| 4,773,097 | 9/1988 | Suzaki et al. | 128/665 |
| 4,821,117 | 4/1989 | Sekiguchi | 600/178 |
| 4,885,634 | 12/1989 | Yabe | 600/109 |
| 5,105,269 | 4/1992 | Nakamura et al. | 600/109 |
| 5,196,928 | 3/1993 | Karasawa et al. | 600/109 |
| 5,213,673 | 5/1993 | Fujimiya et al. | 356/344 X |
| 5,255,087 | 10/1993 | Nakamura et al. | 600/109 |
| 5,413,108 | 5/1995 | Alfano | 128/665 |
| 5,494,483 | 2/1996 | Adair | 600/111 |
| 5,507,287 | 4/1996 | Palcic et al. | 128/665 |

*Primary Examiner*—John P. Leubecker
*Attorney, Agent, or Firm*—Greenblum & Bernstein, P.L.C.

[57] ABSTRACT

A fluorescence diagnosis endoscope system used to observe human tissue is provided. The system has a light source for illuminating the human tissue with normal light and excitation light having a certain wavelength range. The human tissue fluoresces in response to illumination with the excitation light. The system further has a pair of image receiving elements for outputting image signals corresponding to received optical images. A filter which transmits only light produced by the fluoresced human tissue is provided in front of one image receiving element. The image signals output by the image receiving elements are selectively processed and transmitted to a display.

14 Claims, 13 Drawing Sheets

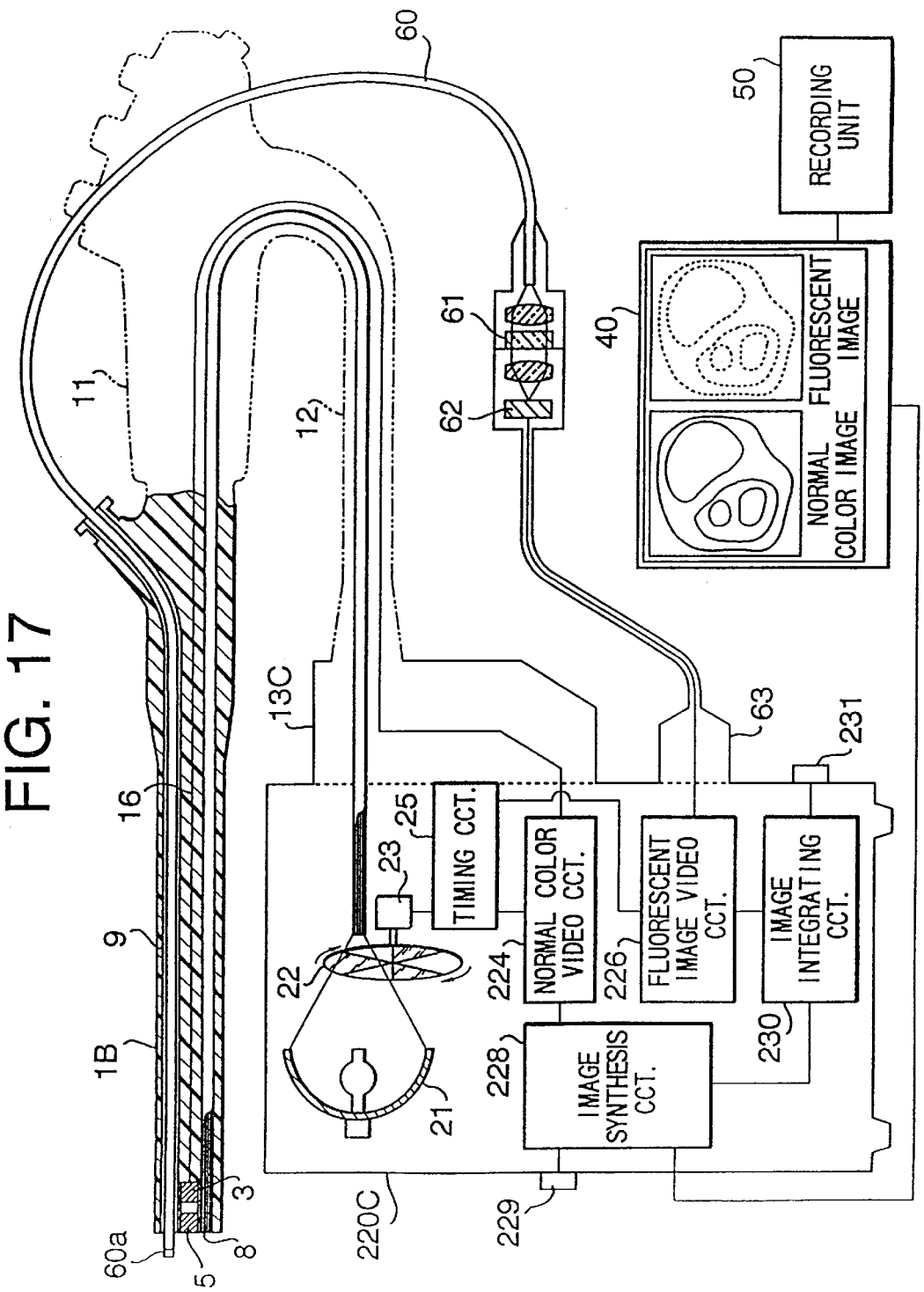

FLUORESCENCE DIAGNOSIS ENDOSCOPE SYSTEM

This application is a continuation of application Ser. No. 08/531,921, filed Sep. 21, 1995, now abandoned.

BACKGROUND OF THE INVENTION

The invention relates to an endoscope system for observing human tissue that is illuminated with light having a predetermined wavelength. More specifically, the human tissue is illuminated with light having a predetermined wavelength, resulting in the tissue fluorescing at another predetermined wavelength. The fluorescence of the tissue is detected and processed by the endoscope system.

It is known that when human tissue is illuminated by light which has a wavelength of between 400 nm (nanometers) and 480 nm (hereinafter referred to as excitation light), the tissue will fluoresce (glow), thereby producing light having an approximate wavelength between 520 nm and 600 nm. Cancerous human tissue, however, does not fluoresce even if it is illuminated with the excitation light. Therefore, cancer at an early stage, which may not be detected during a normal endoscope observation, can be detected with an endoscope system which illuminates the tissue with the excitation light (i.e., a fluorescence diagnosis endoscope system).

A conventional fluorescence diagnosis endoscope system has an excitation light filter between a light source and a light path of an endoscope, and a fluorescent light filter between an objective optical system and an image receiving element provided at the insertion side of the endoscope. The excitation light filter allows only the excitation light to pass through, and the fluorescent light filter allows only the fluorescent light to pass through. An example of such an endoscope system is disclosed in a Japanese Patent Provisional Publication HEI 4-150845.

Since the intensity of the light produced by the fluorescence of the illuminated tissue is low, it is sometimes difficult to obtain a fluorescent image of the tissue that is sufficiently bright. Therefore, it is difficult to perform the diagnosis accurately.

Further, due to the construction of the conventional fluorescence diagnosis endoscope system described above, only the light produced by the fluorescence of the tissue enters the image receiving element of the endoscope. Thus, the organs or the tissue cannot be observed when the tissue is illuminated with normal light by the same endoscope. In order to examine the organs or tissue using normal light, the endoscope for the fluorescence diagnosis is removed and another endoscope for the normal observation is inserted. This is both time consuming and disruptive during an examination of a person.

SUMMARY OF THE INVENTION

It is therefore a first object of the invention to provide an improved endoscope system which is capable of processing the low intensity of the fluorescent light to obtain a bright image, using the fluorescence diagnosis endoscope system.

Another object of the invention is to provide an endoscope system capable of improving the facility of observation of the person when both the fluorescence diagnosis and the diagnosis with the normal light are performed.

A further object of the invention is to provide an endoscope capable of outputting image signal sufficient to perform diagnosis when the fluorescence image is received.

A still further object of the invention is to provide an endoscope system in which general purpose endoscope is utilized to configure the fluorescence diagnosis system.

A further object of the invention is to provide a video processing unit to which either a general purpose endoscope or an endoscope for the fluorescence diagnosis can be connected.

For the above objects, according to an aspect of the invention, there is provided a fluorescence diagnosis endoscope system used to observe human tissue, the system including a light source for illuminating the human tissue with light having a plurality of wavelength ranges, the human tissue fluorescing in response to illumination with excitation light. The excitation light has a predetermined wavelength range within the plurality of wavelength ranges. The system also includes a pair of image receiving elements, each of the pair of image receiving elements outputting an image signal corresponding to an optical image. An objective optical system for forming optical images of the human tissue is provided on each of the pair of image receiving elements, and a filter for transmitting light produced by the fluoresced tissue is arranged between one of the pair of image receiving elements and the objective optical system. Also included is a device for selecting one of the pair of image receiving elements, a device for processing the image signal output by each one of the pair of image receiving elements, and a device for outputting a video signal output by the selected one of the pair of image receiving elements. With this endoscope system, human tissue can be observed using a normal image and a fluorescence image without exchanging the endoscope. Therefore, the facility of observing the person can be improved.

The predetermined wavelength of the excitation light is preferably in a range between 400 nm and 480 nm. Further, the light emitted by the fluoresced tissue has a wavelength in a range between 500 nm and 600 nm.

The endoscope system can be constructed such that the light source illuminates the object with red, green and blue light, and the blue light is used as the excitation light. Therefore, another light source for emitting the excitation light is not required.

Alteratively, the light source can be constructed such that a lamp and a plurality of filters respectively transmit light having different wavelengths, with one of the plurality of filters transmitting only the excitation light. For example, the system may be provided with a red, green and blue filter as well as the filter for transmitting the excitation light. Generally the transmission wavelength range of the blue filter is 400 nm–500 nm. The excitation light filter can be a filter having the transmission wavelength range of 400 nm–480 nm. According to this range, the fluorescent light filter can be a filter having a wider transmission wavelength range of 480 nm–600 nm.

According to another aspect of the invention, there is provided an endoscope for receiving fluorescent light emitted by an object including an image receiving element for receiving an image of the object and for outputting an image signal corresponding to the received image. The image receiving element includes a device for amplifying the image signal, an objective optical system for forming the image of the object on the image receiving element, and a device for transmitting light having a predetermined wavelength range to the object for illuminating the object. The object producing the fluorescent light has another predetermined wavelength range, in response to illumination with light having the predetermined wavelength range. A filter is provided between the image receiving element and the objective optical system for transmitting light having the another predetermined wavelength range, and for not transmitting light having the predetermined wavelength range. Therefore, according to this system, even if the intensity of the fluorescent light emitted by the human tissue is relatively low, it can be dealt with and a bright fluorescence image can be obtained.

Optionally, the image receiving element comprises an amorphous silicon multi-layer amplified MOS imager.

Alternatively, the image receiving element includes a CCD associated with an image intensifier.

Further, the image intensifier is capable of changing its sensitivity, and the sensitivity is set relatively low when the object emits light having a wavelength range outside the range between 500 nm to 600 nm, while the sensitivity is set relatively high when the object emits the wavelength range between 500 nm to 600 nm. According to a further aspect of the invention, there is provided a fluorescence diagnosis endoscope system including an electronic endoscope for receiving an image of an object to be observed and for outputting an image signal corresponding to the received image. A light source is provided for illuminating the object with light having at least one of a plurality of wavelength ranges. The light source illuminates the object with an excitation light having a predetermined wavelength range, and the object fluoresces in response to illumination by the excitation light. The system also includes a fiber scope for inserting into an instrument channel of the electronic endoscope, the fiber scope having a lens at a tip for converging the light from the object and for transmitting the light through the fiber scope. Also included is an image receiving element for receiving the light transmitted through the fiber scope, and a filter provided between an end of the fiber scope opposite the tip and an other image receiving element, the filter transmits light emitted by the fluoresced object and does not transmit light having the predetermined wavelength range. A device for receiving the image signal output by the image receiving element and outputting a corresponding video signal is also provided.

According to this system, the conventional endoscope only having an image receiving element for the normal image is used, and the fluorescence image can also be observed without exchanging the endoscope.

According to still another aspect of the invention, there is provided an endoscope including a pair of image receiving elements for receiving images and for outputting image signals corresponding to the received images, an objective optical system for forming the images on the image receiving elements, and a device for transmitting light having a predetermined wavelength range to illuminate an object. The object fluoresces in response to illumination with the transmitted light. A filter is provided between one of the image receiving elements and the objective optical system for transmitting light emitted by said fluoresced object and for preventing transmission of light reflected by the object. According to this system, since the endoscope has two image receiving elements for the normal image and for the fluorescence image, and the image receiving elements output respective image signals, the normal image and the fluorescence image can be selectively observed without exchanging the endoscope.

According to a further aspect of the invention, there is provided a video processing unit for an endoscope including:

a first and a second image signal processing circuits, each of the image signal processing circuit being capable of receiving an image signal transmitted from an image receiving element of an endoscope, the first and the second image signal processing circuits having different characteristics. Thus, depending on the condition of light which is incident to an image receiving element of an endoscope, the first and the second image signal processing circuit is selectively used.

Optionally, the first image signal processing circuit can receive image signals representative of a plurality of frames corresponding to a plurality of components of light, and output a frame of a color video signal.

BRIEF DESCRIPTION OF THE ACCOMPANYING DRAWINGS

FIG. 17 is a block diagram illustrating the endoscope system shown in FIG. 16.

DESCRIPTION OF THE EMBODIMENT

Figure 1:
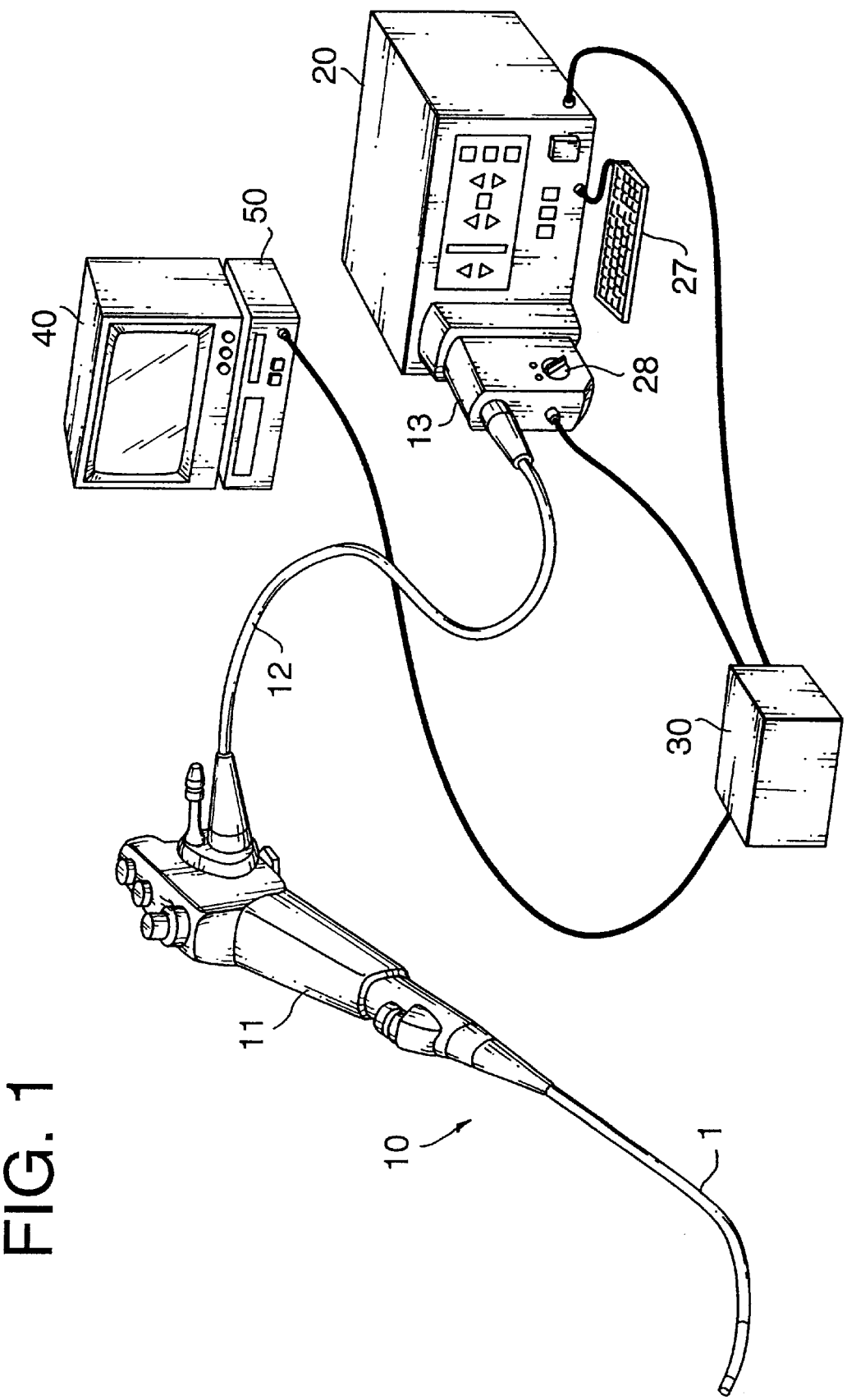
FIG. 1 shows a fluorescence diagnosis endoscope system as a first embodiment of the invention.
Figure 2:
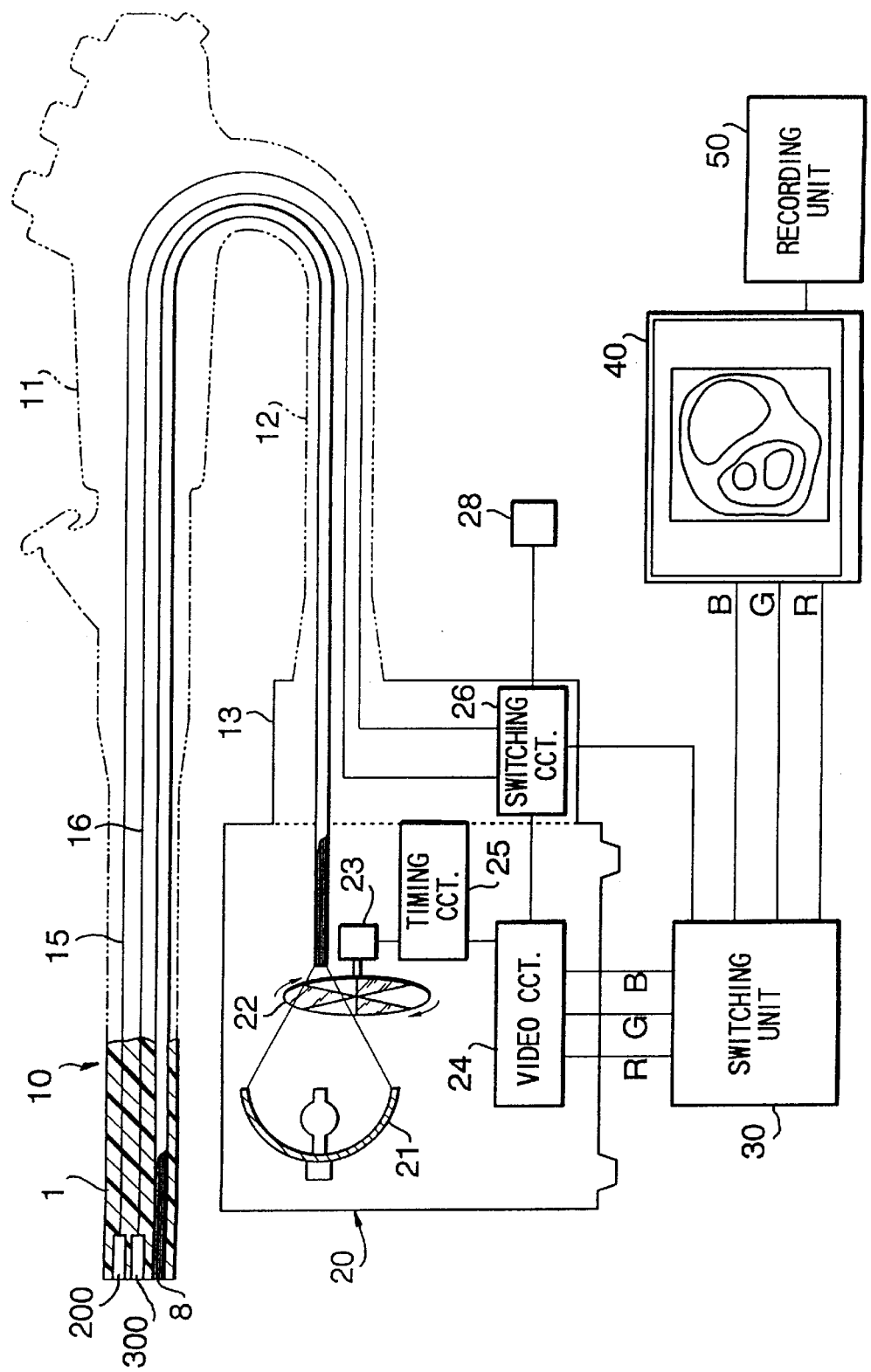
FIG. 2 is a block diagram illustrating the endoscope system of FIG. 1.

FIG. 1 shows a fluorescence diagnosis endoscope system according to a first embodiment of the invention. FIG. 2 is a block diagram illustrating the endoscope system of FIG. 1.

As shown in FIG. 1, the endoscope system is provided with an electronic endoscope 10, a video processing unit 20, a switching unit 30, a display unit 40, and a recording unit 50.

The endoscope 10 has a flexible tube 1 which is inserted inside a human body to be observed, and an operation section 11 which controls the operation of the endoscope 10.

Figure 3:
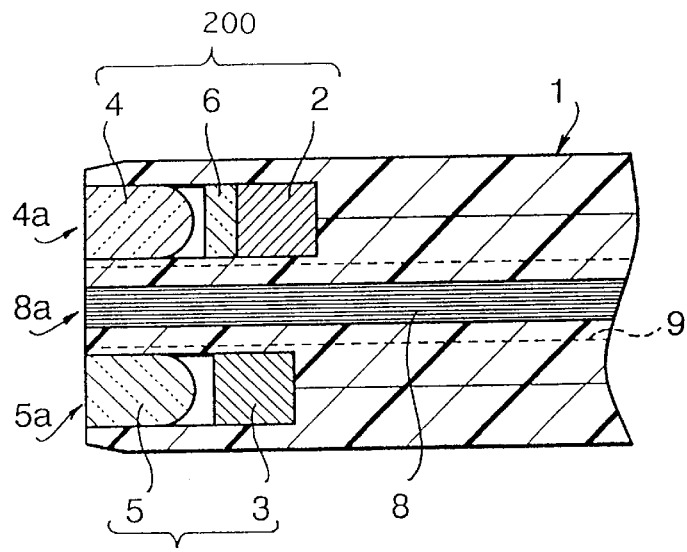
FIG. 3 shows a schematic top view of the insertion side portion of the endoscope used in the endoscope system of FIG. 1.

As shown in FIGS. 2 and 3, at the insertion end portion of the tube 1, first and second optical units 200 and 300 are provided. The optical units 200 and 300 respectively include a first image receiving element 2 and a second image receiving element 3. In the first embodiment, the first and second image receiving elements 2 and 3 are monochromatic CCDs (Charge Coupled Devices). FIG. 2 is not an actual cross-sectional view, but shows the relationship between the optical units 200 and 300 with respect to the entire system. The actual cross-sectional arrangement of the image receiving elements 2 and 3 as well as other elements described below, are shown in FIG. 3.

In front (on left-hand side of FIG. 2 or FIG. 3) of the first and second image receiving elements 2 and 3, a first optical system 4 and a second optical system 5 are provided. The first and second optical systems 4 and 5 form images of an object to be observed on the first and second image receiving elements 2 and 3, respectively.

A fluorescent light filter 6 is located between the first optical system 4 and the first image receiving element 2. No such filters are provided between the second objective optical system 5 and the second image receiving element 3. The fluorescent light filter 6 has a transmission wavelength range greater than the wavelength of the excitation light, thereby preventing the excitation light from being transmitted therethrough. In the following embodiments, the transmission wavelength of the fluorescent light filter 6 is between 520 nm (nanometers) and 600 nm.

A light guide fiber bundle 8 is provided in the endoscope 10. The light emitting surface of the light guide fiber bundle 8 is arranged adjacent to the first and second optical systems 4 and 5, and emits light towards the object (i.e., tissue) to be observed.

Figure 4:
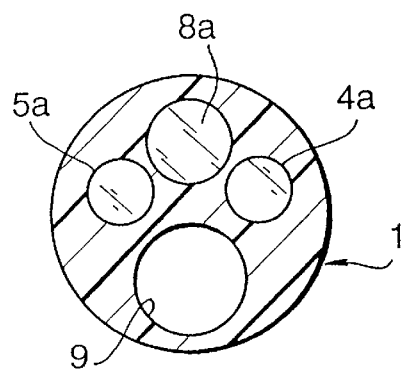
FIG. 4 is a front view of the insertion side portion of the endoscope used in the endoscope system of FIG. 1.

FIG. 4 is a front view of the insertion end of the tube 1. Light receiving windows 4a and 5a are formed on the incident surface of the insertion end of the tube 1, in front of the first and second optical systems 4 and 5, respectively. A light emitting window 8a is also formed on the incident surface of the insertion end of the tube 1, in front of the light emitting end of the light guide fiber bundle 8. A channel 9 is formed through the tube 1, where forceps or operational instruments can be inserted.

As shown in FIG. 1, the tube 1 is connected to the operation section 11. The operation section 11 is connected to the video processing unit 20 through a flexible cable 12 and a connector 13.

A first cable 15, a second cable 16 and the light guide fiber bundle 8 are inserted through the tube 1, the operation section 11, and the flexible cable 12. The first and second cables 15 and 16 transmit signals between the video processing unit 20, and the first and second image receiving elements 2 and 3.

As shown in FIG. 2, a light source 21, which includes a Xenon lamp and a reflector, is provided in the video processing unit 20. Light emitted by the light source 21 enters a light receiving surface of the light guide fiber bundle 8. A disk-shaped RGB (Red, Green and Blue) filter 22 is provided in the light path between the light source 21 and the light receiving surface of the light guide fiber bundle 8.

Figure 5:
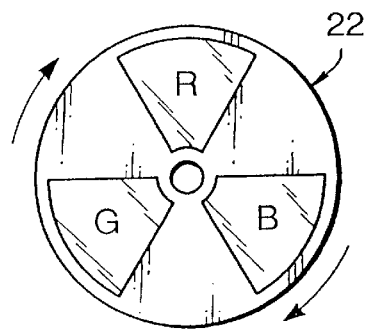
FIG. 5 is a front view of a light filter.

FIG. 5 shows a front view of the RGB filter 22. The RGB filter 22 is constructed such that red, green and blue filter sectors are arranged about an axis of rotation of the filter 22 with light shielding portions provided between the filter sectors. The transmission wavelength ranges for the red, green and blue filter sectors employed in the embodiments described below, are as follows: Each filter sector has a transmissivity of greater than 50 percent for light having a wavelength within the transmission wavelength range. The red filter sector has the transmission range of 580–650 nm; the green filter sector has the transmission range of 500–580 nm; and the blue filter sector has the transmission range of 400–500 nm. The RGB filter 22 is rotated at a constant speed by a motor 23. As the RGB filter 22 rotates, the object to be observed, which is located in front of (i.e., on the left-hand side of FIG. 2) the insertion end of the tube 1, is illuminated by red, green and blue light, sequentially and periodically.

The first and second cables 15 and 16 are connected to a switching circuit 26 provided in the connector 13. The switching circuit 26 is connected with a manually operable selector 28. The selector 28 connects one of the cables 15 and 16 to a video circuit 24 in order to process a normal image signal. A foot switch can also be used as the selector 28.

The first and second image receiving elements 2 and 3, and the motor 23 are driven synchronously with each other in accordance with an output signal of a timing circuit 25. Thus, an image of the object is detected using an RGB frame-sequential method.

The video circuit 24 receives the image signals transmitted from the light receiving elements 2 and/or 3, and outputs RGB color video signals in order to display a color image of the object to be observed, on the screen of the display unit 40.

In the first embodiment, the RGB video signals are transmitted to the display unit 40 through the switching unit 30. The switching unit 30 has two modes of operation. In the first mode of operation, all the RGB signals are transmitted to the display unit 40. In the second mode of operation, the B (blue) signal (when the object is illuminated with the blue light) is transmitted to the display unit 40. The first mode of operation allows the normal color image to be displayed, while the second mode of operation allows the fluorescence image of the object to be displayed on the screen of the display unit 40.

The display unit 40 is connected with the recording unit 50 which records the video signal onto a magnetic recording medium, such as a video tape. The video processor 20 is connected to a keyboard 27 for inputting various operational commands.

In the endoscope system described above, the R, G, and B components of the image signals are output by the first and second image receiving elements 2 and 3, as the RGB filter 22 rotates. Therefore, by connecting the second cable 16 to the video circuit 24 through the switching circuit 26, a normal color video signal is output from the video circuit 24. Therefore, in the first mode of operation of the switching unit 30, all the RGB signals are transmitted to the display unit 40, and the normal color image is displayed on the screen.

The first light receiving element 2 outputs an image signal corresponding to the light having a wavelength approximately between 520 nm and 600 nm, since only the light which passed through the fluorescent light filter 6 is incident on the first light receiving element 2.

Figure 6:
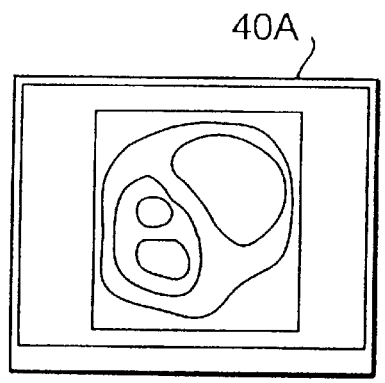
FIG. 6 shows an image seen on a monitor of fluoresced tissue.

When the switching circuit 26 connects the first signal cable 15 to the video circuit 24, and controls the switching unit 30 to operate in the second mode of operation, the image signal when the object is illuminated with blue light (having wavelength between 400 nm and 500 nm) is selected. Therefore, the video signal representative of the fluorescent image is transmitted to the display unit 40. Thus, the fluorescent light image 40A is displayed on the screen of the display unit 40, as shown in FIG. 6. In the embodiment, the actual color of the fluorescent light image is green. However, according to the configuration of the system, a blue image is displayed which represents the fluorescent light image.

As described above, according to the first embodiment, both the normal color image and the fluorescence image can be observed with a single endoscope. There is thus no need to change the endoscopes and the operation of the endoscope between operational modes is neither time consuming nor disruptive to the examination of the person. This facilitates, e.g., the early diagnosis of cancer in the body.

Since the system can selectably transmit the RGB video signal, or the fluorescence image video signal to the display unit 40, an off-the-shelf video processing device can be used for the video processing unit 40.

In the first embodiment, the RGB filter 22 has three sectors (filters) which transmit red, green and blue components, respectively, of light when the normal color image is observed. Further, the light transmitted through the blue filter (the blue light) is also used as the excitation light when the fluorescent image is observed.

Figure 7:
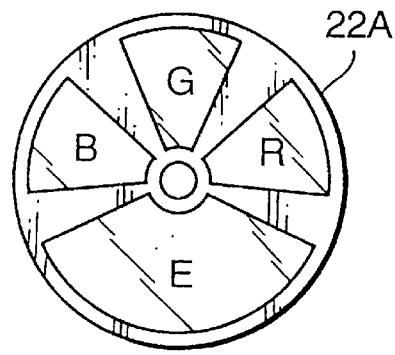
FIG. 7 shows a modification of the light filter shown in FIG. 5.

In a modification to the first embodiment, a modified filter 22A, shown in FIG. 7, is employed. The modified filter 22A has RGB filters and another filter E. Depending on the portion of the human tissue to be observed, the fluorescent light way have a wavelength range between 480 and 500 nm. This range of the fluorescent light overlaps the upper side of the transmission wavelength range of the blue filter. In order to obtain only a fluorescent image of the tissue (and not a normal image), the filter E should have an upper limit of the transmission wavelength range which is lower than the upper limit of the transmission wavelength range of the blue filter (i.e., 500 nm), and lower than 480 nm. The filter E transmits the excitation light having the wavelength between 400 nm and 480 nm. When this modified filter 22A is used, the filter E transmits the excitation light to the object to be observed. When the filter E is used, a filter having the transmission wavelength range of 480–600 nm is used as the fluorescent light filter 6.

Figure 8:
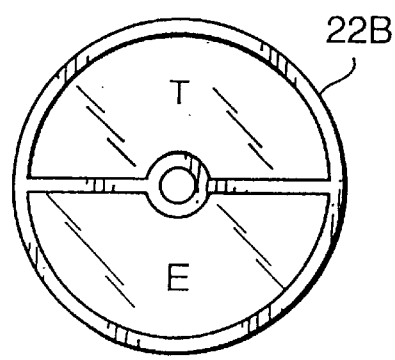
FIG. 8 shows another modification of the light filter shown in FIG. 5.

In a second modification of the first embodiment, the filter 22 is replaced with a modified filter 22B, shown in FIG. 8. Further, in the second modification of the first embodiment, a color image receiving element is used instead of the monochromatic image receiving element 3. The modified filter 22B does not have RGB filters since the color image receiving element does not require such a filter. The modified filter 22B has a transparent filter T (this could also be an opening) and the filter E, for transmitting the excitation light.

Figure 9:
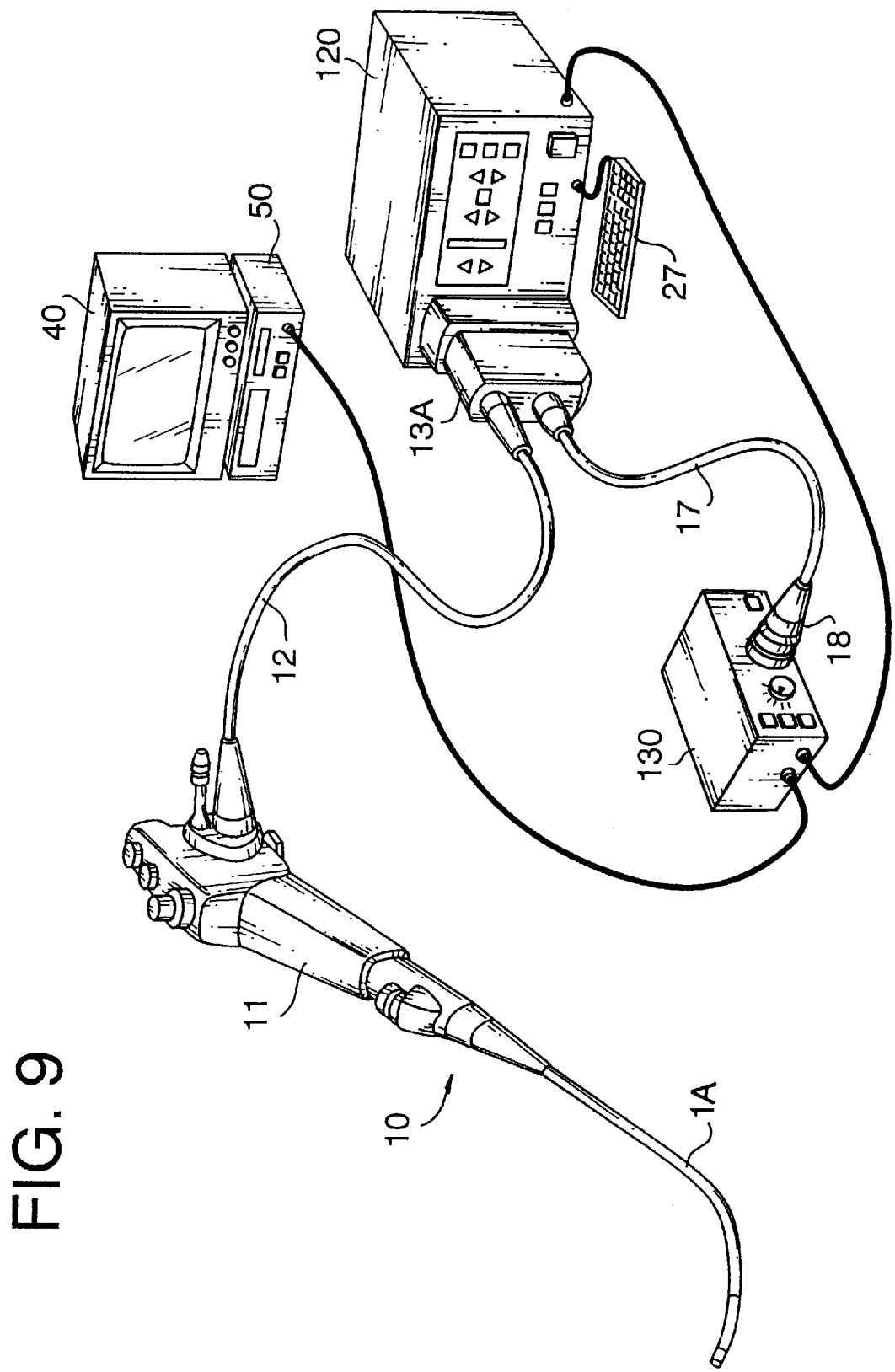
FIG. 9 shows a fluorescence diagnosis endoscope system according to a second embodiment of the present invention.
Figure 10:
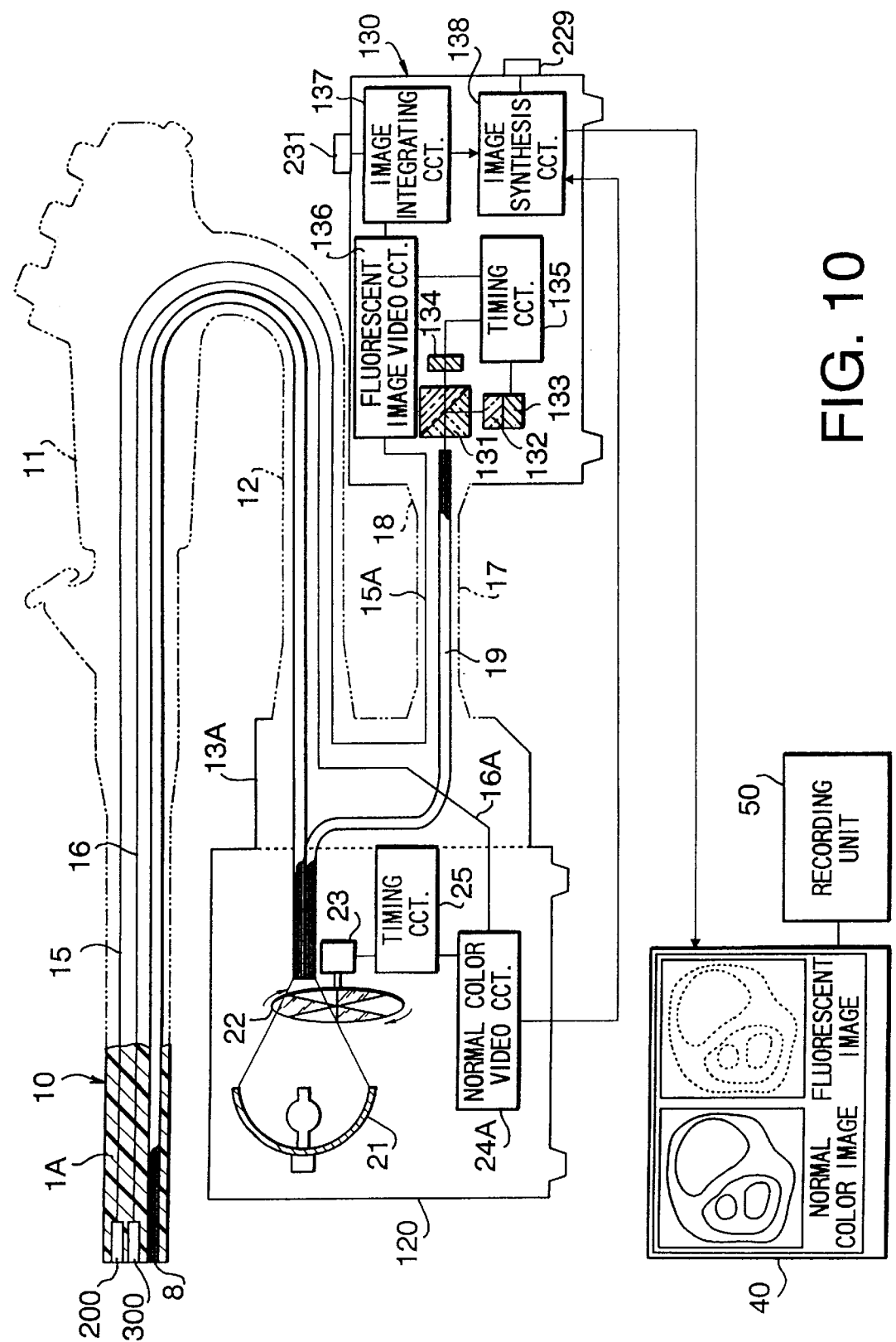
FIG. 10 is a block diagram illustrating the endoscope system shown in FIG. 9.

FIG. 9 shows a fluorescence diagnosis endoscope system according to a second embodiment of the invention, and FIG. 10 is a block diagram illustrating the endoscope system of FIG. 9. In the description, the devices, which are similar to those of the first embodiment have the same reference numerals, and will not be described below.

As shown in FIG. 9, the endoscope system according to the second embodiment includes the endoscope 10, a normal video processing unit 120, a fluorescent light image control unit 130, the display unit 40 and the recording unit 50.

The endoscope 10 is connected to the video processing unit 120 through the flexible cable 12 and a connector 13A. The fluorescent light image control unit 130 is connected to the video processing unit 120 through a connector 18, a flexible cable 17 and the connector 13A.

The video processing unit 120 has the light source 21, the filter 22, the motor 23, and the timing circuit 25 which are similar to those in the video processor 20 of the first embodiment. The video processing unit 120 also includes a video circuit 24A which processes only the image signal output by the second image receiving element 3.

The second image receiving element 3 is connected to the video circuit 24A through the second cable 16, and a cable 16A provided in the connector 13A. The second image receiving element 3 is driven synchronously with the rotation of the motor 23 in accordance with the timing signal output by the timing circuit 25.

The first image receiving element 2 is connected to a video circuit 136 through the cable 15 and a cable 15A, which is provided in the flexible cable 17.

A light guide 19 is provided in the flexible cable 17. The light incident surface of the light guide 19 is arranged adjacent to the light incident surface of the light guide fiber bundle 8. The light emitting side of the light guide 19 is provided inside the connector 18.

In the fluorescence image control unit 130, a beam Splitter 131 is provided such that a light receiving surface thereof contacts the light emitting surface of the light guide 19. Light emitted from the light emitting surface of the light guide 19 is split by the beam splitter 131 into two rays of light. One ray is incident on a first light receiving device 133 through a blue filter 132, and the other ray is incident on a second light receiving device 134. Output signals of the first and second light receiving devices 133 and 134 are transmitted to a timing circuit 135. Thus, the timing circuit 135 and the timing circuit 25 generate the timing signals synchronously with each other.

As described above, the first signal cable 15 is connected to the video circuit 136. As the timing signal is transmitted from the timing circuit 135, the video circuit 136 detects the image signal only when the object is illuminated with a blue light having wavelength between 400 nm and 475 nm. Since the image signal received by the video circuit 136 corresponds to light transmitted through the filter 6, the image is the fluorescence image.

In an image integrating circuit 137, a plurality of frames of the fluorescent light image output by the video circuit 136 is integrated (superimposed) to form a single bright image. Then, the bright image signal is sent to a image synthesis circuit 138. In the second embodiment, the number of frames to be superimposed can be set either manually by means of a switch 231, or automatically.

The image synthesis circuit 138 receives the integrated fluorescent light video signal from the image integrating circuit 137, and the color video signal from the normal video circuit 24A. Then, in accordance with the operated status of a display switch 229, the image synthesis circuit 138 outputs one of the normal color video signal or fluorescence image video signal, or both to the display unit 40.

According to the second embodiment, the first image receiving element 2 is connected to a video processor which is provided separately from the normal video processing unit 120. Further, an off-the-shelf video processor can be used for processing the image observed using the normal color video signal.

Figure 11:
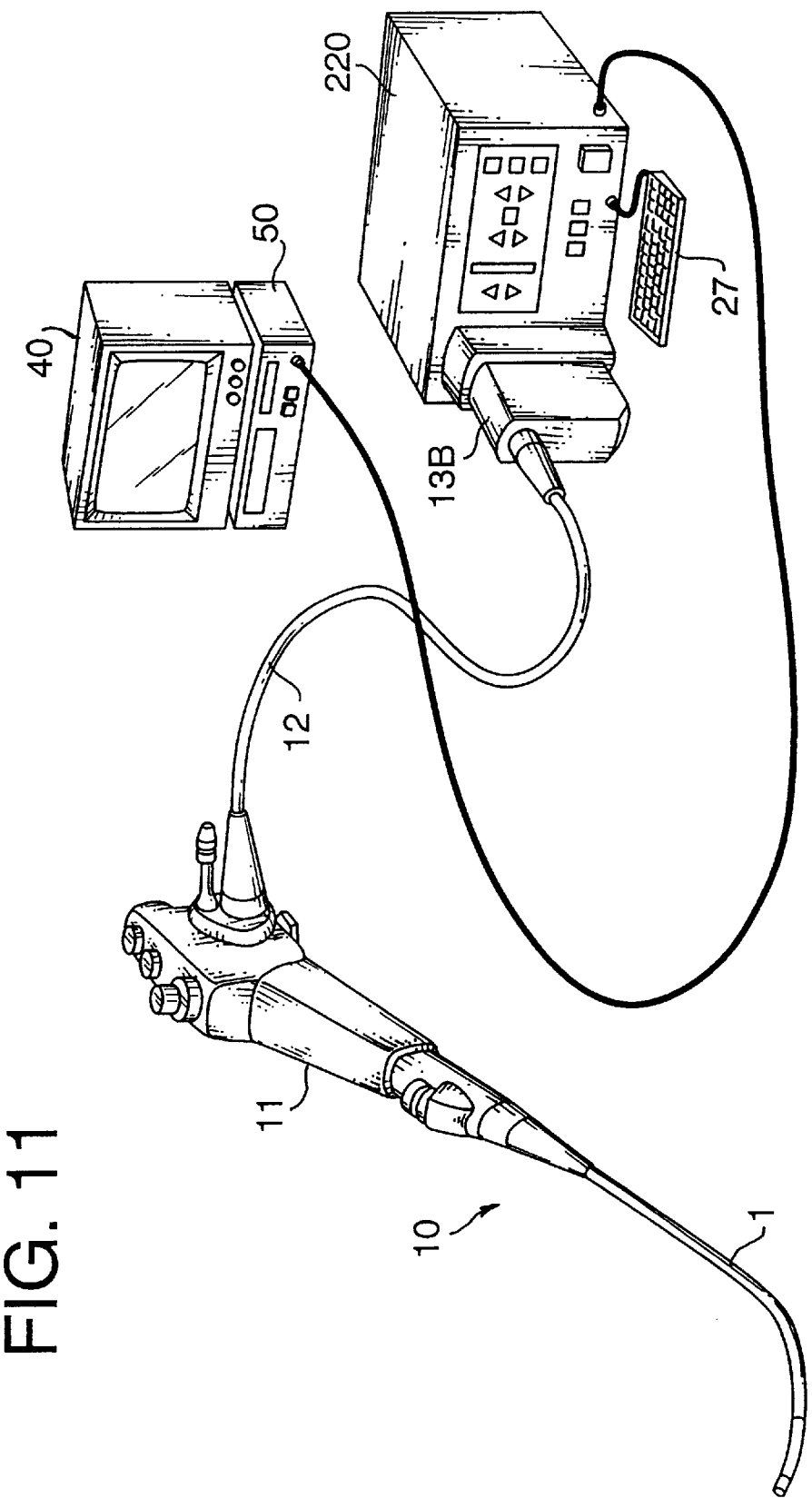
FIG. 11 shows a fluorescence diagnosis endoscope system according to a third embodiment of the present invention.
Figure 12:
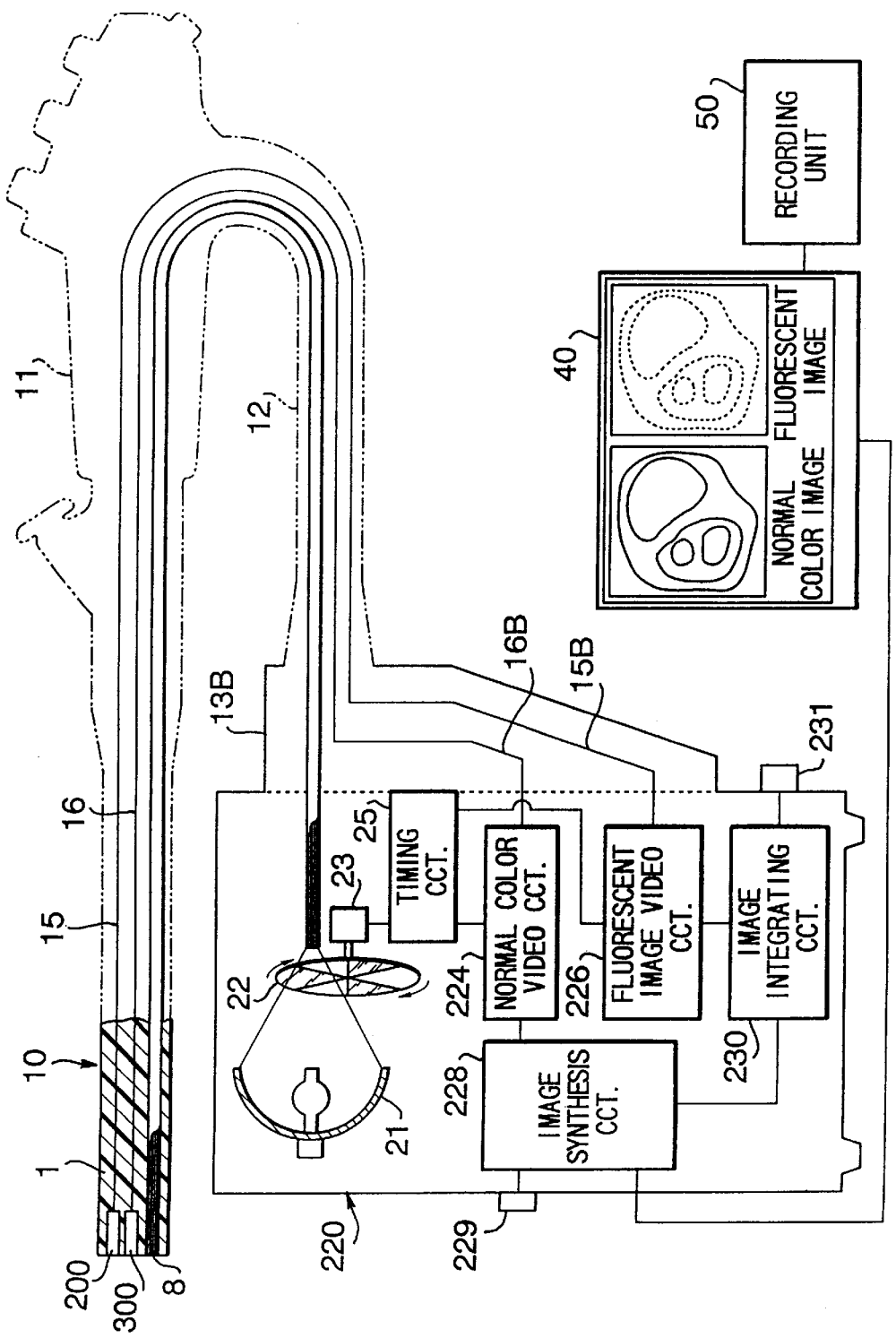
FIG. 12 is a block diagram illustrating the endoscope system shown in FIG. 11.

FIG. 11 shows a fluorescence diagnosis endoscope system according to a third embodiment of the present invention. FIG. 12 is a block diagram illustrating the endoscope system of FIG. 11.

The system of the third embodiment consists of the endoscope 10, a video processing unit 220, the display unit 40 and the recording unit 50. The endoscope 10 and the video processing unit 220 are connected by the flexible cable 12 through a connector 13B. The keyboard 27 for inputting commands etc. is connected to the video processing unit 220.

The light source 21, the filter 22, the motor 23 and the timing circuit 25 are provided in the video processing unit 220. Further, the video processing unit 220 is provided with a video circuit 224 for processing a normal color image, a video circuit 226 for processing the fluorescent light image, an image integrating circuit 230, and an image synthesizing circuit 228. The video circuits 224 and 226, the image integrating circuit 230, and the image synthesizing circuit 228 function in a similar way to the video circuits 24A and 136, the image integrating circuit 137, the image synthesizing circuit 138, respectively of the second embodiment. Therefore, these circuits will not be described in detail.

The first image receiving element 2 is connected to the video circuit 226 through the cable 15 and a cable 15B, which is provided in the connector 13B. The second image receiving element 3 is connected to the video circuit 224 through the cable 16 and a cable 16B, which is provided inside the connector 13B. In accordance with the output signal of the timing circuit 25, the video circuit 226 outputs only the video signal corresponding to the fluorescent light image.

In the third embodiment, the video signal output by the video circuit 226 is integrated by the integrating circuit 230, in a similar manner described for the second embodiment above. The number of frames to be superimposed is set by the manually operable switch 231. By operating a screen switch 229, the image to be displayed on the screen of the display unit 40 can be selected.

In the third embodiment, based on the output signal of the timing circuit 25, the first and second image receiving elements 2 and 3 are driven synchronously with the rotation of the motor 223, and accordingly the RGB frame-sequential image reading is performed.

The video circuit 226 detects the image signal when the object is illuminated with the blue light (having wavelength between 400 nm and 500 nm). Since the filter 6 is provided in front of the image receiving element 2, a fluorescence image video signal is output by the video circuit 226.

The signal output by the video circuit 226 is transmitted to the integrating circuit 230, and a plurality of frames are integrated. The number of frames to be superimposed by the integrating circuit 230 is set automatically, or by the switch 231.

Figure 13:
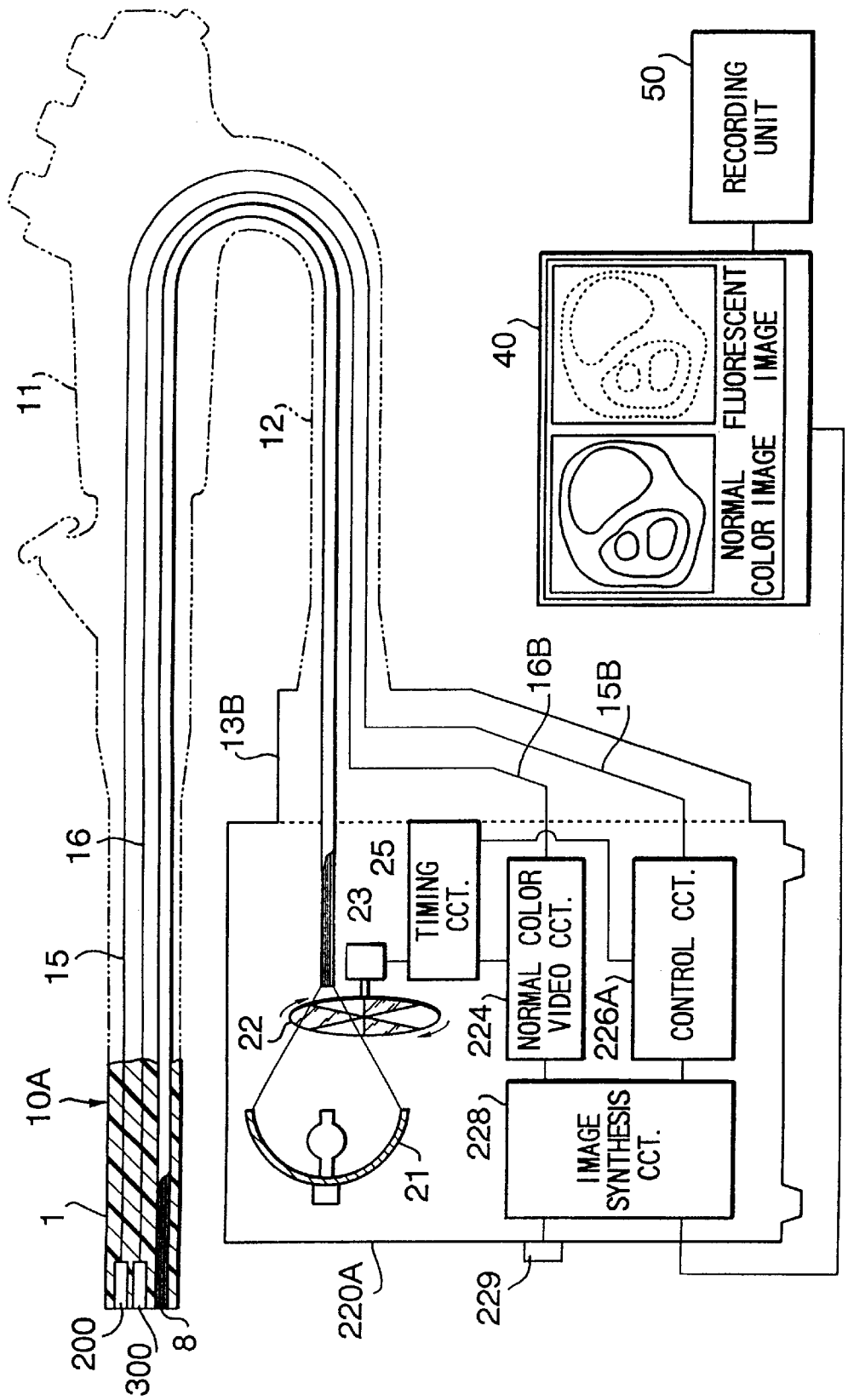
FIG. 13 is a block diagram of a fluorescence diagnosis endoscope system according to a fourth embodiment of the present invention.
Figure 14:
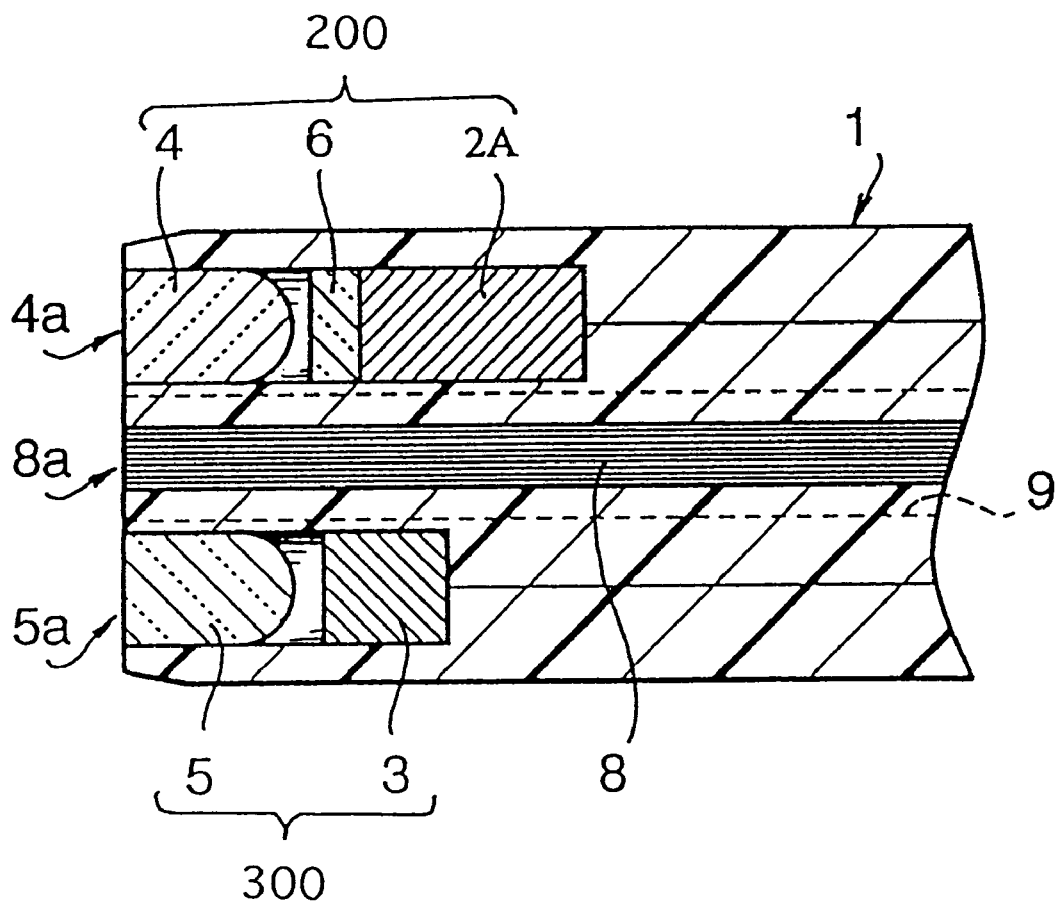
FIG. 14 shows a schematic cross section of the insertion side portion of the endoscope used in the endoscope system shown in FIG. 13.

FIG. 13 is a block diagram of a fourth embodiment of a fluorescence diagnosis endoscope system according to the present invention. FIG. 14 shows a schematic cross-section of the insertion end of the tube 1 of the endoscope used in the endoscope system shown in FIG. 13.

The fourth embodiment consists of an endoscope 10A, a video processing unit 220A, the display unit 40 and the recording unit 50.

The fourth embodiment will be described hereinafter in relation to the third embodiment. In the fourth embodiment, instead of the image receiving element 2 of the foregoing embodiments, a very high sensitivity image receiving element 2A is used in the endoscope 10A. Further, the video circuit 226 and the integrating circuit 230 are replaced with a control circuit 226A for controlling the image receiving element 2A. In the embodiment, the image receiving element 2A transfers electric charge to an amorphous silicon multi-layered amplified MOS imager to amplify the charge by a factor of over one thousand.

The image receiving element 3 is connected to the video circuit 224 through the cable 16 and a cable 16B provided inside the connector 13B to process the normal color image. The image receiving element 2A is connected to the control circuit 226A. The video circuit 224 and the controller 226A are supplied with timing signals from the timing circuit 25, and drive the image receiving element 3 and 2A, respectively, and synchronously with the rotation of the filter 22.

As described above, since the image receiving element 2A has a very high sensitivity, the integrating circuit is not necessary. The circuitry in the fourth embodiment is therefore simplified. Further, the image output to the monitor 40 is sufficiently bright.

Figure 15:
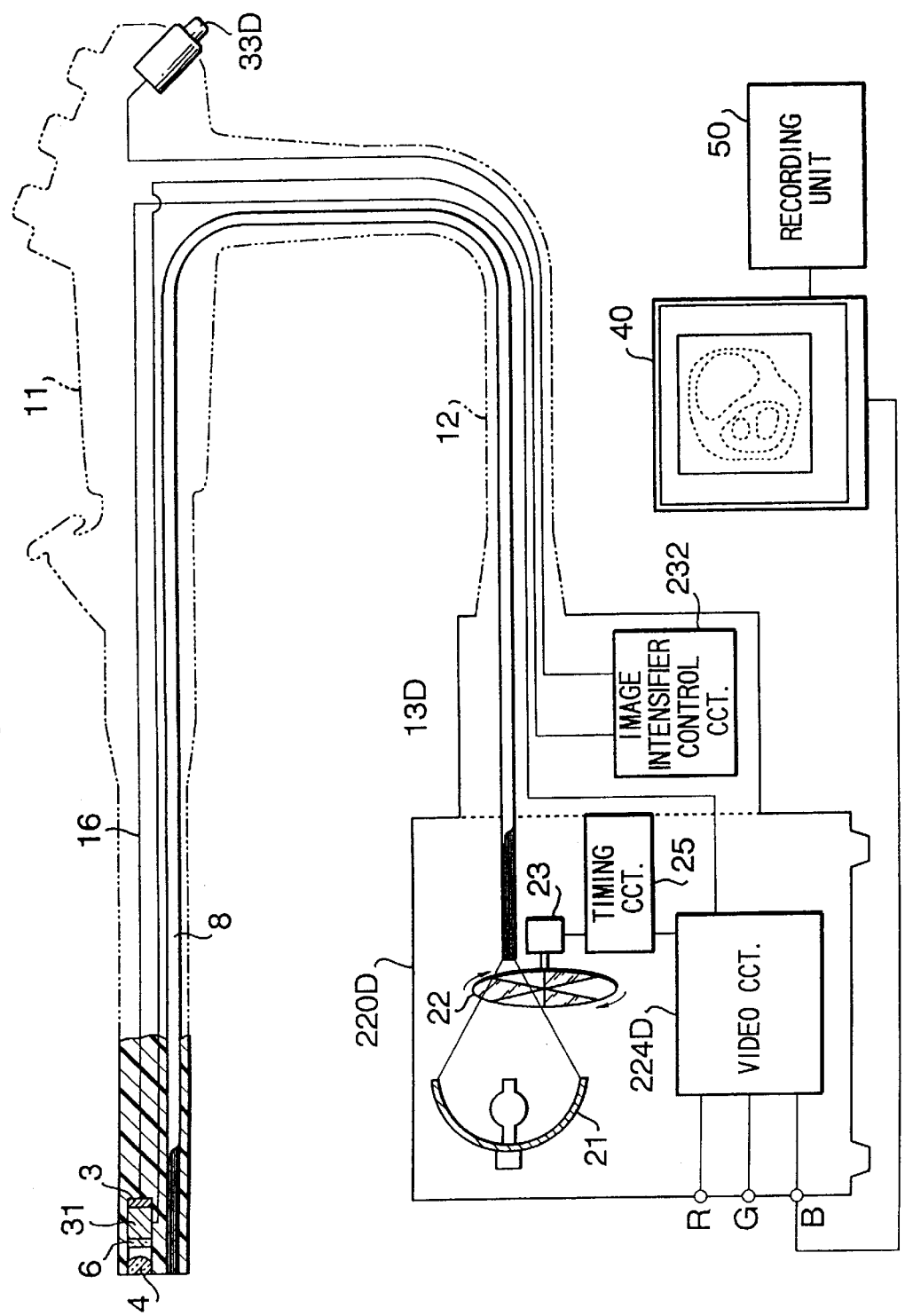
FIG. 15 is a block diagram of a fluorescence diagnosis endoscope system according to a fifth embodiment of the present invention.

FIG. 15 is a block diagram of a fifth embodiment of a fluorescence diagnosis endoscope system according to the present invention.

In the fifth embodiment, an image intensifier 31 is provided in front of (i.e., at the left-hand side of FIG. 15) a conventional image receiving element 3, as shown in FIG. 15. An image intensifier control circuit 232 for controlling the image intensifier 31 is provided inside a connector 13D, and a sensitivity adjusting switch 33D is provided on the operation section 11.

Figure 16:
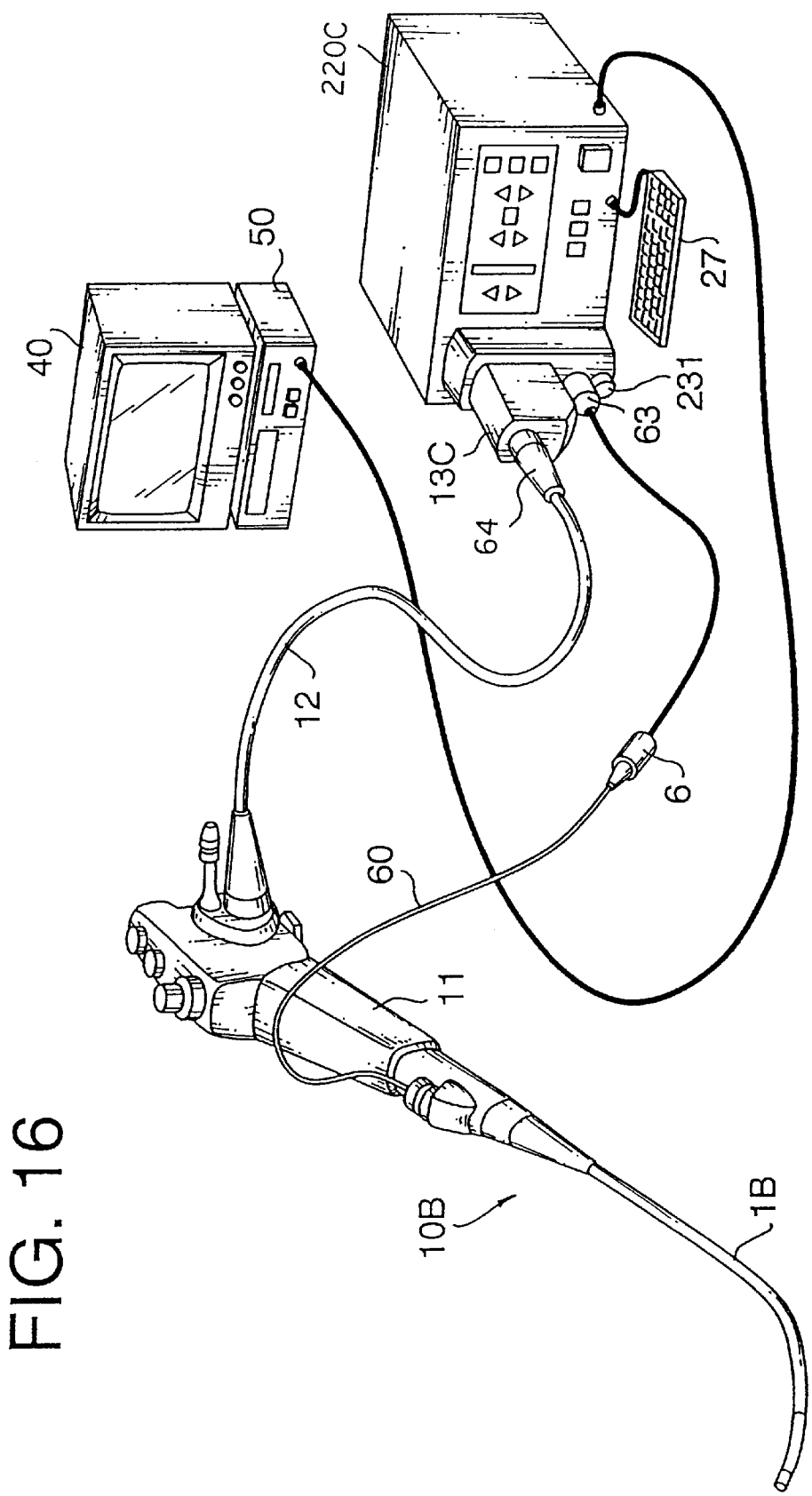
FIG. 16 shows a fluorescence diagnosis endoscope system according to a sixth embodiment of the present invention.

In the fifth embodiment, by changing the sensitivity of the image intensifier 31, the brightness of the image is adjusted. Further, since the signal having the adjusted amplitude is input to the video processing unit 220D, only one video circuit 224D is required, and the construction of the video circuit 224D is simple. Further, similar to the previous embodiments, the video circuit 224D and the image receiving element 3 are driven synchronously with the rotation of the motor 23, in accordance with the timing signal output by the timing circuit 25. FIG. 16 shows a fluorescence diagnosis endoscope system according to a sixth embodiment of the present invention. FIG. 17 is a block diagram illustrating the endoscope system shown in FIG. 16.

The sixth embodiment employs the endoscope 10B, a video processing unit 220C, the display unit 40 and the recording unit 50. Further, the system is provided with a fiber scope 60 which is made of an image guide fiber bundle inserted in the forceps channel 9 of the endoscope 10B. An objective lens 60a is provided at an insertion end of the fiber scope 60. The other end of the fiber scope 60 is coupled to a connector 64. A filter for passing the fluorescent light having a wavelength between 500 nm and 600 nm is provided in the connector 64. Light emitted by the other end of the fiber scope 60 passes through the filter 61 and is incident on a monochromatic image receiving element 62. The image receiving element 62 receives a fluorescent image and transmits an image signal to a video circuit 226 through a connector 63. The function of each element of the video processing unit 220C is the same as the elements described for the video processing unit 220 of the third embodiment, shown in FIG. 12.

The present disclosure relates to subject matters contained in Japanese Patent Applications Nos. HEI 6-226521, HEI 6-226522, HEI 6-226523, HEI 6-226524, filed on Sep. 21, 1994, which are expressly incorporated herein by reference in their entireties.

What is claimed is:

1. A fluorescence diagnosis endoscope system for observing living tissue, said system comprising:
   a single light source for illuminating the living tissue, said single light source emitting light having a plurality of wavelength ranges, said light comprising visible light and an excitation light;
   a filter unit, arranged between said single light source and the living tissue, that periodically filters said light from said single light source, said filter unit comprising at least one blue, at least one red, and at least one green filters, said blue filters blocking light that does not have a wavelength between 400–500 nm, such that said at least one blue filter is the sole source of light that causes the living tissue to fluoresce and emit fluorescent light;

a first optical unit at the tip of an electronic endoscope, said first optical unit comprising a first optical system and a first imaging element for receiving light reflected from the living tissue by light passing through said green, blue, and red filters to illuminate the living tissue and generating first image signals;

a second optical unit provided at the tip of the electronic endoscope for receiving said fluorescent light and generating second image signals, said second optical unit comprising a second imaging element, a second optical system, and a fluorescence filter provided in front of said second imaging element, the fluorescence filter preventing transmission of light having the same wavelength as the excitation light;

an image processor for processing said first image signals and said second image signals, in accordance with the periodical filtering of light by said filter unit, to form a color image of the living tissue and a fluorescence image of the living tissue, respectively; and an output device for outputting said color image and said fluorescence image.

2. The fluorescence diagnosis endoscope system according to claim 1, said output device comprising a selector for selecting at least one of said color image and said fluorescence image for output.

3. The fluorescence diagnosis endoscope system according to claim 2, further comprising a display for displaying said at least one of said color image and said fluorescence image.

4. The fluorescence diagnosis endoscope system according to claim 2, said image processor comprising:

a color image processor for forming said color image; and a fluorescent image processor and an image integrating circuit for forming said fluorescence image, said image integrating circuit integrating a predetermined number of images output by said fluorescent image processor to form said fluorescence image; and an image synthesizer, responsive to said selector, for outputting at least one of said color image and said fluorescence image.

5. The fluorescence diagnosis endoscope system according to claim 2, wherein said second optical unit comprises an image amplifier for amplifying said second image signals prior to output, said image processor comprising:

a color image processor for forming said color image;

a control circuit for forming said fluorescence image based on said second image signals; and an image synthesizer, responsive to said selector, for outputting at least one of said color image and said fluorescence image.

6. A florescence diagnosis endoscope system for observing living tissue comprising:

a single light source for illuminating the living tissue with at least an excitation light that causes the living tissue to fluoresce and emit fluorescent light, said single light source emitting light having a plurality of wavelength ranges, said light comprising visible light and said excitation light;

a filter unit, arranged between said single light source and the living tissue, that periodically filters said light from said single light source, said filter unit comprising at least one red, at least one blue, and at least one green filters that pass light that illuminates the living tissue to obtain an optical image, and said blue filter preventing transmission of light not between 400–500 nm such that said at least one blue filter is the sole source of light that causes the living tissue to fluoresce and emit fluorescent light;

an image receiving element provided at the tip of an electronic endoscope for generating amplified image signals based on a received image of the living tissue;

an optical system for forming said image of the living tissue on said image receiving element;

a fluorescence filter, provided at the tip of the electronic endoscope, and between said optical system and said image receiving element, that transmits said fluorescent light to said image receiving element only when said blue filter is inserted between said single light source and the living tissue, the fluorescence filter preventing transmission of light having the same wavelength as the excitation light; and a control circuit for controlling and driving said image receiving element to output said amplified image signals in accordance with the periodical filtering of light by said filter unit.

7. The florescence diagnosis endoscope system according to claim 6, said image receiving element comprising an amorphous silicon multi-layer amplified MOS imager.

8. The florescence diagnosis endoscope system according to claim 6, said image receiving element comprising a CCD and an image intensifier.

9. The endoscope system of claim 8, further comprising a signal output unit for outputting video signals corresponding to the color image of the living tissue and the fluorescence image of the living tissue, and a display unit for displaying the color image of the living tissue or the fluorescence image of the living tissue based on the video signals provided as output from the signal output unit.

10. A fluorescence diagnosis endoscope system for observing living tissue comprising:

a single light source;

a light transmitting member, which transmits said light emitted by said single light source toward the living tissue;

a plurality of filters sequentially inserted in an optical path between said single light source and said light transmitting member to filter said light emitted by said single light source, said plurality of filters comprising at least one red, at least one blue, and at least one green filter, said red filters preventing transmission of light not having a wavelength between 580–650 nm, said blue filter preventing transmission of light not having a wavelength between 400–500 nm, and said green filter preventing transmission of light not having a wavelength between 500–580 nm;

said at least one blue filter being the sole source of light that causes the living tissue to fluoresce and emit fluorescent light;

a fluorescent filter;

a first imaging element that receives light reflected from said living tissue; and a second imaging element receiving fluorescent light emitted from said living tissue and passing through said fluorescent filter.

11. The endoscope system of claim 10, wherein said first imaging element is mounted at the at the tip of an electronic endoscope.

12. The endoscope system of claim 10, wherein said second imaging element is mounted at the at the tip of an electronic endoscope.

13. The endoscope system of claim 10, further comprising:

said first imaging element emitting a color image signal;

said second imaging element emitting a fluorescent image signal;

a selector for selecting one of said color and fluorescent image signals; and an image processor, responsive to said selector, for processing said color image signal and said fluorescent image signal in accordance with the sequential filtering by said plurality of filters to form a color image of the living tissue and a fluorescence image of the living tissue, respectively.

14. The endoscope system of claim 10, further comprising a rotating disk upon which said red, blue and green filters are mounted.

* * * * *

UNITED STATES PATENT AND TRADEMARK OFFICE
CERTIFICATE OF CORRECTION

PATENT NO.    : 6,099,466
DATED         : August 8, 2000
INVENTOR(S)   : H. Sano et al.

It is certified that error appears in the above-identified patent and that said Letters Patent is hereby corrected as shown below:

<u>Title page,</u>
Item [56], References Cited, the following U.S. PATENT DOCUMENTS should be included:

-- 5,318,024    6/1994    Kittrell et al.
       Re. 31,815    1/1985    Alfano --

The following FOREIGN PATENT DOCUMENTS should be included:

-- JP        4150845    5/1992
       JP        3500373    1/1991
       W.I.P.O.   8902718    4/1989
       JP        654792     3/1994
       E.P.O.     0512965A1  11/1992 --

The following OTHER PUBLICATION should be included:

-- KATO, "A Fluorescence/Imaging Diagnostic and Therapeutic System using Excimer Dye Laser", with English translation thereof. --

Signed and Sealed this

Twenty-seventh Day of May, 2003

JAMES E. ROGAN
*Director of the United States Patent and Trademark Office*